(12) United States Patent
Haswell

(10) Patent No.: US 6,179,819 B1
(45) Date of Patent: Jan. 30, 2001

(54) UMBILICAL CORD BLOOD COLLECTION

(76) Inventor: John N. Haswell, 1255 N. Gulfstream Ave., Apt. 508, Sarasota, FL (US) 34236

( * ) Notice: Under 35 U.S.C. 154(b), the term of this patent shall be extended for 0 days.

(21) Appl. No.: 09/392,252

(22) Filed: Sep. 9, 1999

(51) Int. Cl.[7] .................................................. A61B 19/00
(52) U.S. Cl. ........................ 604/356; 604/400; 604/408; 128/854; 600/573
(58) Field of Search .................................. 604/319, 329, 604/331, 339, 346, 347, 356, 355, 357, 323, 400, 408; 128/849, 850, 852, 854, 855; 383/11, 14; 606/119, 120, 167; 600/573, 583

(56) References Cited

U.S. PATENT DOCUMENTS

| | | |
|---|---|---|
| 3,494,356 | 2/1970 | Melges . |
| 3,589,365 | 6/1971 | Sejman . |
| 3,646,938 * | 3/1972 | Haswell . |
| 3,654,924 * | 4/1972 | Wilson et al. . |
| 3,722,502 | 3/1973 | Besuner et al. . |
| 3,762,399 | 10/1973 | Reidell . |
| 3,800,790 | 4/1974 | Collins . |
| 3,955,569 * | 5/1976 | Krzewinski et al. . |
| 4,051,845 * | 10/1977 | Collins . |
| 4,076,017 * | 2/1978 | Haswell . |
| 4,105,019 | 8/1978 | Haswell . |
| 4,149,537 | 4/1979 | Haswell . |
| 4,164,941 * | 8/1979 | Knopick et al. . |
| 4,169,472 * | 10/1979 | Morris . |
| 4,204,527 | 5/1980 | Wu et al. . |
| 4,265,118 | 5/1981 | Griesel . |
| 4,489,720 | 12/1984 | Morris et al. . |
| 4,890,628 | 1/1990 | Jackson . |
| 4,974,604 | 12/1990 | Morris . |
| 5,148,940 * | 9/1992 | Mendise ................................ 128/849 |
| 5,174,305 | 12/1992 | Childs . |
| 5,322,071 * | 6/1994 | Ambrose ............................... 128/849 |
| 5,342,328 * | 8/1994 | Grossman et al. .................... 604/317 |
| 5,345,946 * | 9/1994 | Butterworth et al. ................ 128/853 |
| 5,368,583 | 11/1994 | Fleury . |
| 5,503,163 * | 4/1996 | Boyd .................................... 128/849 |
| 5,618,278 * | 4/1997 | Rothrum .............................. 604/356 |
| 5,916,202 | 6/1999 | Haswell . |

OTHER PUBLICATIONS

Eder et al. "A New Device for Collecting Cord Blood", *Obstetrics & Gynecology,*. 86(5):850–852 (1995).

VIACORD. "Cord Blood Banking", Viacord Brochures with attached abstracts, Sep. 1995, 6 pages.

International Cord Blood Foundation. "Commonly Asked Health Care Questions." International Cord Blood Foundation Brochure, 6 pages.

CBR Collection Kit. "Quick Review: Steps for the Collection of Cord Blood with the CBR Collection Kit." CBR, 2 pages.

* cited by examiner

Primary Examiner—Sharon Kennedy
Assistant Examiner—Michael M Thompson
(74) Attorney, Agent, or Firm—Browdy and Neimark

(57) ABSTRACT

A device and method for the collection of umbilical cord blood during obstetrical delivery are disclosed. A pouch is attached to an obstetrical drape in a location convenient for filling with cord blood. The pouch includes a canal for the umbilical cord to be inserted into the pouch, and a sealing closure. The pouch may contain an anti-coagulant. One embodiment includes multiple compartments with various blood-treatment substances. After filling the pouch is closed and removed from the drape. The blood can be used for a variety of hematologic laboratory tests and for long term cryo-preservation for a stem cell transfusion to infants and adults.

2 Claims, 4 Drawing Sheets

UMBILICAL CORD BLOOD COLLECTION

CROSS-REFERENCE TO RELATED APPLICATIONS

The present application is related to U.S. application Ser. No. 08/707,963, filed Aug. 30, 1996, now U.S. Pat. No. 5,916,202, issued Jun. 29, 1999.

FIELD OF THE INVENTION

The present invention relates to devices and methods for the collection of umbilical cord blood.

BACKGROUND OF THE INVENTION

Recently, umbilical cord blood—the blood left in the umbilical cord and placenta after birth—has been recognized as a life-saving substance. The reason is that umbilical cord blood, like bone marrow, contains regenerative "stem" cells. Stem cells are the primitive cells from which other blood cells—white cells, red cells, and platelets—develop. Thus, they are the building blocks of the immune and blood cell systems. Cord blood stem cells are unique in that they are immature "naive" immune cells. When they are used in transplantation, they have reduced reactivity and are less likely to recognize the recipient as foreign. When transplanted into a sick person, even a single stem cell has the ability to regenerate the person's blood system. For this reason, stem cells are vital when a person's immune system has been weakened by radiation or chemotherapy, or by diseases that attack the immune system. Stem cells are highly effective against many diseases.

Since the potential of the stem cells in bone marrow has been recognized, about four thousand deaths per year are being prevented by bone marrow transplants. However, bone marrow is in short supply; the shortage of bone marrow amounts to 10,000–15,000 transplants per year that cannot be performed. As cord blood also contains regenerative "stem" cells, it is being used as an alternative to bone marrow. The number of cord blood transplants increased tenfold between 1994 and 1995. Many lives could be saved if umbilical cord blood were routinely banked and its additional stem cells became available for transplants.

Moreover, cord blood is much more effective than bone marrow for several reasons:

(1) It is less likely to trigger an adverse reaction when transplanted. The incidence of GVHD (Graft versus Host Disease) is about five times lower with cord blood as compared to bone marrow when the donor and recipient are unrelated (up to 90% GVHD for marrow, less than 20% with cord blood). When the donor and recipient are siblings, the rate of GVHD is ten times lower (2% for cord blood as compared to 20% for marrow). The engraftment rate for cord blood transplants is 85% overall.

(2) Cord blood stem cells are 8 to 11 times more "prolific" than bone marrow cells, and so better regenerate the body's blood system.

(3) Cord blood stem cells are better for gene herapies.

(4) No invasive procedures are needed to obtain ord blood.

(5) Cord blood is less likely to contain viruses than is bone marrow from adult donors, who have had a lifetime to acquire diseases.

Adults as well as children have been successfully treated with cord blood, and cord blood can be cryo-preserved in liquid nitrogen and remain usable for years. If a child's cord blood is preserved in this way, the grown individual can use his or her own stem cells later in life to fight various serious diseases. After age two, an individual's own cord blood is the most effective transplant material since it is less likely to be rejected than another individuals.

Cord blood is effective against numerous genetic and blood diseases and has the potential to become a valuable treatment for many others. Diseases which are now treatable with cord blood include: malignancies (leukemia, myeloma, and neuroblastoma); aplastic anemia; XKP; SCIDS; Wiskott-Aldrich Syndrome; thalessemia; Fanconi anemia; plasma cell disorders and inherited erythrocyte abnormities. At present, the majority of cord blood transplants are used to treat leukemia. Research is now under way on using cord blood to combat rheumatoid arthritis, AIDS, multiple sclerosis, sickle cell anemia, cancer of the lung and colon, and Hodgkin's lymphoma.

The International Cord Blood Foundation is promoting conservation and banking of cord blood. It is expected that greater awareness by physicians and expectant parents will increase the amount of retrieved cord blood and the number of lives saved. The National Institutes of Health, too, is spending millions of dollars to promote cord blood use.

However, the technology for extracting cord blood presents obstacles and obstructs the rapid acceptance of routinely banking all cord blood. The main problems are in (1) the convenience of collecting the blood and (2) obtaining an adequate amount of blood for both testing and banking.

Because there are so many uses for banked cord blood, because some therapies require large amounts, and because the cost of transporting and storing larger amounts as compared to smaller amounts is minimal, it is clear that the maximum possible amount of cord blood should be collected and stored. However, as will be seen from the discussion below, the present methods do not get all the available blood out of the umbilical cord.

The present standard delivery room protocol includes collecting and sending a small sample of umbilical cord blood to the laboratory shortly after delivery of the fetus for a variety of tests, including, but not limited to, hemoglobin, hematocrit, blood type and Rh factor, and antibody tests. Other laboratory studies on the cord blood specimen that could be performed include blood chemistries, blood cultures, HIV testing, testing for use of illegal drugs, such as cocaine, by the mother, lactate levels, blood gases such as oxygen and arbon dioxide saturation levels, and other studies.

Historically, this has been accomplished by attempting to direct a cord blood stream into opened laboratory test tubes and then capping the test tubes. Usually, spillage of cord blood occurs during this procedure, which is difficult for one person to perform.

The blood spillage is doubly bad because it not only wastes the precious blood but also increases the health workers' exposure to a potential HIV hazard. To decrease the amount of spilled blood, a funnel might be provided. However, to support a funnel and a test tube having a stopper while dripping blood would be even more awkward than merely filling a test tube. The used funnel would be another piece of contaminated trash. The test tube also ends up as contaminated trash and, if made of glass, it presents a puncture hazard in the event of breakage.

After a test tube or test tubes are filled with the desired amounts of blood and taken away, the attending pediatricians frequently call for a laboratory technician to come to the delivery room or newborn nursery soon after the birth to perform additional venipunctures or heel sticks on the newborn infant to obtain more blood samples for base line studies about the condition of the infant. These additional intrusions could of course be avoided by performing the same tests on cord blood, if more were available. However, the test tubes are gone by that time.

To collect larger amounts of cord blood for later tests or for long term preservation, the primitive and messy method of dripping blood into test tubes is too inefficient. At the present time bulk umbilical cord blood collection is performed mainly by using 50 cc syringes that contain a heparinized solution. The syringes are sent to pregnant women in the form of a kit. The expectant mother or parents are then responsible for bringing the kit to their delivery. The syringes, with needles attached, are given to the delivering doctor.

After delivery of the infant and cutting and clamping the cord the physician inserts the needle into the distal umbilical cord vein and slowly aspirates all available cord blood into the syringes. These syringes are then labeled for identification, needles are removed, the ends are capped, and they are placed into a zipper-locking plastic bag or bags. The bag is placed into an insulated mailing box, and they are mailed to a central processing laboratory. The syringes must be kept at room temperature through these steps.

This method requires a long time (about five minutes) and a substantial amount of effort. Three or four syringes are used (each being capped, labeled, etc.) and the needles must be inserted at numerous places along the cord for best results; each insertion site must be swabbed prior to sticking with the needle. Literature on this method (Cbr Collection Kit brochure) teaches against any manipulation of the umbilical cord; the cord is laid out on a tray and the needles stuck in a various places in an attempt to collect sufficient blood. The average amount collected is 80 cc of cord blood.

The yield is low because, first, blood is drawn only from the single umbilical cord vein, and not from either of the two arteries, and second, because the collection efficiency of applied suction is low (as is discussed further below)

Besides the large amounts of time and effort required, and the low yield, this method of collecting cord blood is dangerous because of the several needles that need to be uncovered, used, removed, and disposed of, and the because of the numerous sticks into the thin-walled umbilical vein of the slippery cord. The syringes, tray, and needles constitute a great deal of hazardous waste material and/or extra cleaning and sterilizing work.

A different sort of prior-art collection apparatus is disclosed by Eder et al, in U.S. Pat. No. 5,342,328 and in an article in *Obstetrics and Gynecology*. Their "umbilicup" device, made by MKMI of Encino, Calif., is a rigid cylindrical container with a removable top lid and a funnel-shaped interior baffle. The umbilical cord is cut at both ends and placed into the container, which includes a guarded needle communicating with, and extending downward from, the container. The rubber stopper of an evacuated test tube is forced onto the needle, and the vacuum draws off blood pooled in the funnel-shaped bottom of the container.

The umbilicup avoids the use of uncovered needles, but has numerous drawbacks; the greatest is that the collection efficiency of the umbilicup is quite low. The cord is merely piled into the container, and blood drips into the bottom. Blood in the many looped parts of the cord is trapped, never reaches the bottom of the container, and never is collected. The amount of blood the umbilicup collects from an entire cord is only 6.1 cc (mean)+/−3.1 cc (one standard deviation), with about 2 more cc if heparin is added; in other words, a maximum of about 11 cc. In some cases the umbilicup collects less than one cc of blood, and the collected blood can be as little as 0.4 cc. Without the addition of heparin, there is insufficient blood for testing in almost 3% of uses.

Like syringes, the umbilicup is relatively expensive and creates bulky contaminated plastic waste and dirty needles. While faster than the painstaking needle suction method, the use of the umbilicup still requires additional handling and table space and time must be allowed for the blood to drip into the bottom of the container. As with the primitive drip method, the test tubes can present a puncture hazard if made of glass.

Another disadvantage of the umbilicup is that the pooled blood contacts the outside of the cord, which is more likely to be contaminated than the inside of the cord. Thus, the risk of the collected cord blood being contaminated is greater.

SUMMARY OF THE INVENTION

It is a primary object of the present invention to collect and contain one specific and special body fluid, umbilical cord blood, and to collect larger quantities than have been collected by the prior-art methods and apparatus.

Another object of the invention is to easily, effectively, and without spillage, direct this blood into a single container or into multiple containers that are compartmentalized.

It is still another object of the invention to render the blood suitable for a variety of different laboratory tests, or for long term cryo-preservation, for example by mixing the blood with specialized ingredients.

It is a further object of the invention to prevent the spread and spillage of cord blood during the procedure of delivery and of collecting cord blood.

It is also an object of the invention to satisfy OSHA requirements relating to body fluids and universal precautions, and to collect cord blood without the use of needles and without producing contaminated waste.

It is still a further object of this invention that the several pouches and containers which are used, can be easily sealed prior to hand off, so as to effectively contain without spillage any of the cord blood.

It is also an object of this invention to contain the blood in pouches that can be easily released from obstetrical drapes and handed off to other personnel so that they may be readily transferred for transport to distant facilities for cryo-preservation or be sent locally for short term storage or laboratory examination.

Accordingly, the present invention has an object, among others, to overcome deficiencies in the prior art such as noted above, including but not limited to: avoiding additional intrusions on the infant's body for more blood samples; avoiding blood spillage during cord blood collection; and effecting universal precautions.

The present invention provides pouches or containers, of stationary or pull-down type, to be positioned at an advantageous-immediate position so that as soon as the cord is clamped and the infant is handed off to the attending staff, the delivering physician or midwife can expeditiously place the distal end of the umbilical cord into one or more of these containers. The physician or midwife can then immediately and effectively, and without spillage (utilizing universal precautions), collect samples—or the entire amount—of the remaining cord blood. The blood can be extracted by gravity and/or by "milking" the umbilical cord.

The pouch of the invention is preferably attached to a surgical drape in a position below, but not centered on, the mother's buttocks, so that gravity will assist in removing the cord blood. However, the pouch should not be too far below the table edge because the umbilical cord is of limited length.

The pouch may also be provided separately from the drape for attachment to the drape by the physician at the time of delivery. For this purpose, such a pouch would be provided with adhesive, such as an adhesive strip with a peel-off protective cover.

The "milking" process is performed by the physician placing the index finger and thumb around the umbilical cord as close as possible to the insertion of the cord into the placenta proper and gently pulling downward so as to force any remaining cord blood to extrude out of the distal end. Unlike the prior-art collection devices and methods, the present invention's pouch holds the end of the umbilical cord so that the cord can be milked easily using two hands.

This procedure is able to draw blood out of the placenta as well as the cord itself. Hand squeezing as practiced in the present invention can produce a greater blood pressure, at the squeezed area of the cord, than can suction produced by needle aspiration. Suction is actually air pressure, which is limited to 15 psi. The greater local pressure exerted by a hand in milking the cord moves the viscous cord blood through small-diameter vessels better than suction alone is able to. The milking hand, as it moves toward the severed end of the cord, tends to produce a vacuum in the cord behind it, which adds the blood-moving effect of suction to the primary positive pressure effect for even greater flow.

In addition, the high pressure below the squeezing hand distends the vessels for faster flow and so a greater volume of collected blood. In contrast, the prior-art suction method constricts the upstream vessels and so reduces the flow; the greater the applied suction, the greater the constriction. The suction method therefore cannot produce as much cord blood as can milking the cord.

After being filled, the pouch or pouches can then be sealed to avoid spillage, released from their position on the under-the-buttock delivery drape, and handed off to a technician for transportation to long-term storage or a local laboratory.

The pouch contains the appropriate solutions, powders, pellets, or products to effect appropriate preservation for laboratory analysis, such as liquid or freeze dried lithium-heparin salts, sodium citrates, oxylates, etc.

If the sealed cord blood specimen is to be processed for long term cryo-preservation storage, the collection device may contain a citrate or heparin-type additive before the blood is sent to a medical service company to further process the cord blood. At the medical service company the specimen is spun down and the stem cells or "buffy coat" are processed and further concentrated for long term cryopreservation.

The collected cord blood specimen can also be refrigerated at the local hospital or delivery facility to be available should the attending pediatrician desire additional base line studies. Blood gases are one of the more frequently performed baseline tests. Stored cord specimens are available for additional studies.

One embodiment of the present invention includes multiple pouches that collect various cord blood specimens. The pouches may be so constructed so that a single specimen of cord blood is directed into multiple compartments, i.e., four or five different separate pouches for different tests.

Preferably, the present invention includes these features:

(1) The collection pouches/containers are made of disposable plastic.

(2) The pouches are preferably affixed to the obstetrical drape with adhesive or other means. They may be affixed to the drape before or after the drape is placed into position for the delivery.

(3) The pouches are preferably affixed to the type of delivery drape generally called the "under-the-buttock drape".

(4) The pouch is affixed in a position offset from the midline of the drape so as to avoid contamination by any maternal blood that extrudes from the vagina prior to delivery, after delivery, or during collection of cord blood.

(5) A common feature of many under-the-buttock drapes is an upward fold at the portion designed to lie under the buttocks of the patient when in use as is shown, for example, in the embodiment of FIG. 3. Pockets may be formed in this fold for insertion of the hands of the obstetrician or other attending person to push the drape into position beneath the patient without touching the patient. The pouch may be affixed in a position immediately below the free end of the folded portion of the under-the-buttock drape so that the top of the pouch is covered by the end of the drape. In this manner the pouch will be partially hidden and protected from any maternal blood or contamination.

(6) The pouch is labeled near the dependent portion "Pull Downwardly before Insertion of Umbilical Cord" or with some similar message.

(7) The pouch is labeled near the dependent portion "Tear off Pouch At Completion-Secure Pouch Closure" or with some similar message.

(8) A flap near the top of the pouch is labeled "Pull Up and Insert Cord" or with some similar message.

(9) The upper portion is labeled "Tear Off Here-Perforated Area" or with some similar message.

BRIEF DESCRIPTION OF THE DRAWING

The above and other objects and the nature and advantages of the present invention will become more apparent from the following detailed description of embodiments, taken in conjunction with drawings, wherein.

DETAILED DESCRIPTION OF PREFERRED EMBODIMENTS

Here, and in the following claims:

"birth" means natural birth or induced birth and includes both Caesarean and vaginal deliveries;

"cord" means umbilical cord unless otherwise stated;

"drape" is any flaccid covering;

"pouch" is any container, including non-flaccid (eg., semi-rigid) containers;

"removably mounted" means either (1) having a first portion that is permanently attached and second portion that can be separated from the first portion, as by tearing; or (2) being removable as a whole, for example by the use of sticky adhesive or hook-and-loop fastener;

"sufficiently large" means large enough to admit the object to be admitted, but not substantially larger than is necessary for that purpose;

"zipper", "zip closure", "zipper seal", and like terms mean a linear press-closure which holds together by interference between two linear elements of either side of the seal, with or without a movable closure element, such as those sold under the trademark ZIPLOC.

Figure 1:
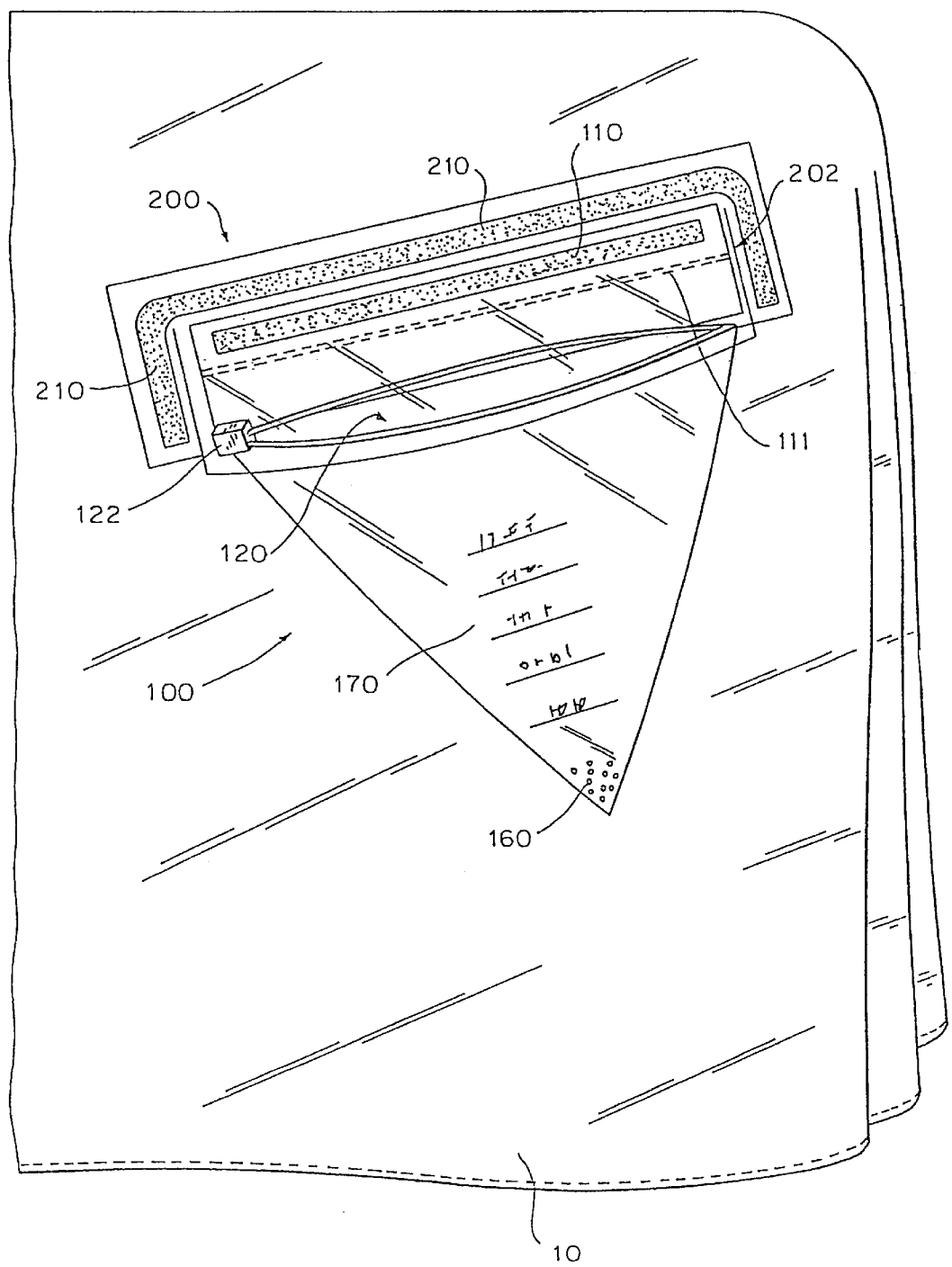
FIG. 1 is a perspective view of a first preferred embodiment of the invention.

FIG. 1 shows one embodiment of the present invention, a device for collecting umbilical cord blood. The device includes a collection pouch 100 removably mounted on an obstetrical drape 10. The drape is flaccid, preferably of waterproof sheet plastic material. The pouch 100 is preferably also of flaccid material, for example transparent plastic. Both the drape 10 and the pouch 100 may be made of the same material or the pocket can be made of any convenient plastic material and affixed to the material of the drape. The pouch may be formed in any manner and in any outline shape other than the triangular shape shown in FIG. 1.

The pouch 100 may alternatively be rigid or semi-rigid, but flaccid containers have the advantage over rigid containers that they are less bulky prior to use (since they fold up) and are also less bulky when full because they can assume any shape and because the excess air can be squeezed out. They also use less material and are stronger for their weight.

The pouch 100 is removably attached to the drape 10 by an attachment 110. The attachment 110 is preferably weak enough that the pouch can be removed by breaking the attachment 110. If, conversely, the attachment is strong, a perforation 111 is provided to allow the remainder of the pouch 100 below the attachment 110 to be removed. Instead of a perforation, the invention may have a thinned or otherwise weakened tear line, a second layer of adhesive, or the like, for separating the pouch proper from the attachment portion 110. The attachment 110 may be by sticky adhesive, thermal or sonic welding, staples, hook-and-loop fasteners, or any other conventional means for attachment.

The means for removably holding the collection pouch in its mounting position on the drape—the attachment 110 and/or tear line 111—allow the pouch 100 to be held conveniently on the drape 10 but also to be easily removed from the drape once the pouch 100 is filled with cord blood and sealed. The pouch 100 is preferably mounted on a portion of the drape 10 that is "dependent" (hanging down) from the edge of the delivery table when the drape 10 is used. The preferred type of obstetrical drape for use in the present invention is the "under-the-buttocks" drape that is disposed under the pregnant mother's buttocks during the delivery, with the dependent portion hanging down from the adjacent edge of the delivery table. Preferably, the mounting position of the pouch 100, on the outside surface of the drape 10, is such that when the drape 10 is in use the pouch 100 is perhaps one foot below the table edge (on the hanging or dependent end of the drape 10) and slightly offset, preferably to the right side (toward the right hand of the attending physician or nurse who faces the end of the table). In this position the pouch 100 is in a very convenient position for inserting the umbilical cord and at a height below the table for gravity-assisted drainage.

Figure 3:
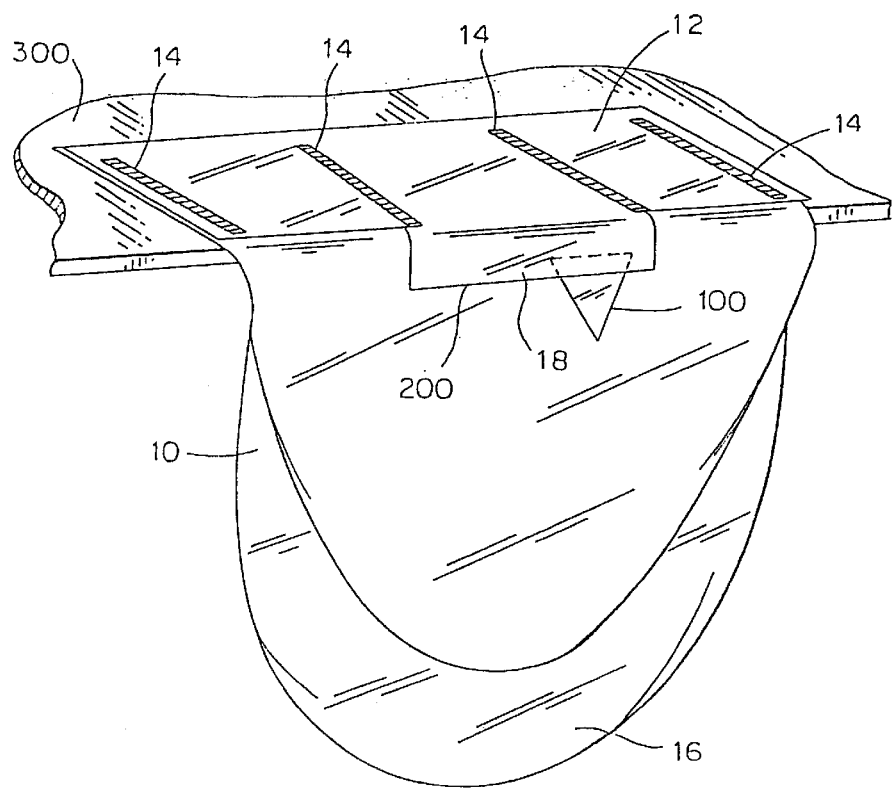
FIG. 3 is a perspective view of another embodiment of the invention showing the position of the pouch.

FIG. 3 shows the position of the drape 10 and pocket 100 when the drape is in use on an obstetrical table 300. The drape 10 shown in FIG. 3 is of the type having a folded overlay at the end which is disposed over table 300 and is intended to lie under the buttocks of the patient when in use. The folded over portion 12 forms an insert into which the hands of the obstetrician or other attending personnel may be placed in order to push the drape 10 into position under the buttocks of the patient without actually touching the patient. The drape may include seams 14 which form pockets on either side for the placement of the hands of the person placing the drape. The drape may also be formed a pouch 16 for collecting postpartum fluid loss as is known for example from U.S. Pat. Nos. 4,076,017, 4,105,019, and 4,149,537.

A flap 12 may conveniently extend beyond the edge of the table when in use so as to depend downwardly therefrom as shown at 18 in FIG. 3. This flap 18 may be only an extension of the center portion of the overlay 12 or may be an extension of the entire width of the overlay 12. This dependent portion 18 may conveniently cover the top of the pouch 100 so as to protect the opening of the pouch from any postpartum fluids which may be deposited on the drape. The flap 18 may be easily raised when access to the opening of the pouch 100 is desired.

Figure 5:
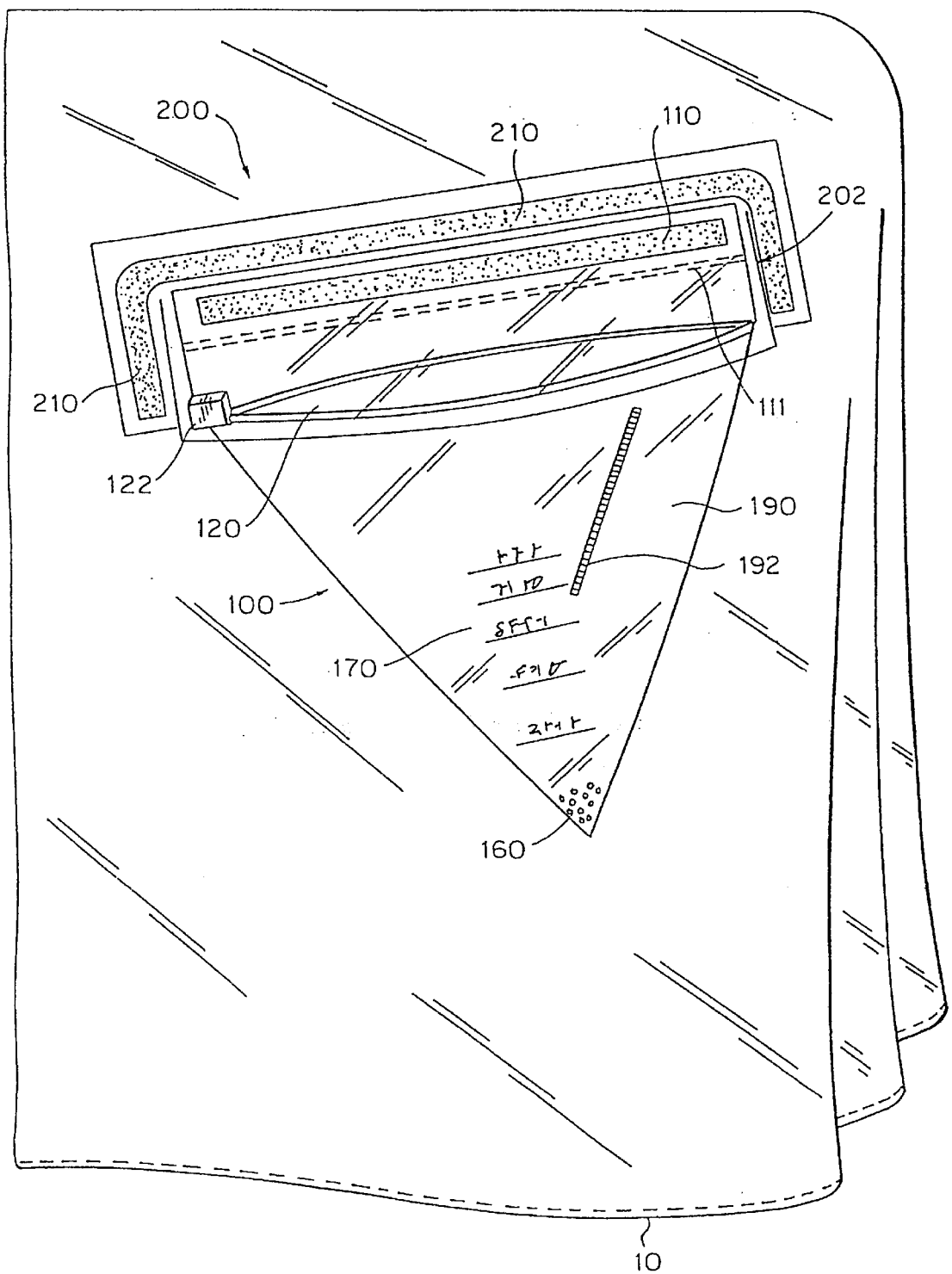
FIG. 5 is a perspective view of a variation on the first preferred embodiment of the invention.

The pouch 100 includes an opening 120 sufficiently large to admit a human umbilical cord; it may extend across the entire top end, as shown in FIG. 1. In an alternative embodiment (shown in FIG. 5) the opening 120 may include a cord canal 190 formed by welding a seam 192 parallel to an edge of the pouch 100 and at a distance to make the canal sufficiently large for easy insertion of an umbilical cord into the canal.

Cord blood collected and stored in the pouch 100 should be sterile and uncontaminated. The off-midline position of the pouch 100 on the drape 10 helps to prevent contaminants from running over the pouch 100, but for extra protection the interior and opening 120 of the pouch 100 should remain sterile. For this purpose, a flap 200 may optionally be provided. The flap 200 is preferably of the same sort of flaccid or flexible material as the drape 10 and/or pouch 100, and is continuously joined to the drape 10 (alternatively to the pouch 100) along an attachment line 210 above the opening 120, which resists liquid penetration. The flap 200 diverts any contaminated body fluids or substances, which may run down the drape 10 away from the opening 120.

The flap 200 may preferably, as shown in FIG. 1, be attached to the drape along an attachment line 210 in the shape of an inverted U; this protects the opening 120 from runoff from the sides as well as above. The flap 200 may include pleats 202 which allow it to be easily pulled up to expose the opening 120 for insertion of the cord. The flap attachment 210, like the attachment 110 of the pouch, may be of any sort and may optionally allow for the flap to be removed with a strong pull.

When using the invention, in order to maintain sterility of the pouch 100 and of the collected cord blood the attending physician, nurse, or midwife will preferably disinfect the distal end of the umbilical cord, (i.e., the end farthest from the placenta) that is to be inserted into the opening 120. One method is to clamp the cord at two places several inches apart near the baby; to disinfect the outside surface of the cord between the two clamps; to sever the cord with a sterile instrument, close to the clamp that is distal the placenta and within the sterilized area; and then with sterile gloves to insert the severed end of the cord into the opening 120.

After the insertion, the cord preferably is then "milked" by using the hand or an instrument to squeeze down upon the cord and then move the squeezing hand or instrument away from the placenta toward the pouch 100. This will remove from both the cord and the placenta the maximum available amount of cord blood because the milking strokes, combined with the natural resilience of the arteries and veins in the cord, will create a partial vacuum in the placenta and draw blood from it to the cord and thence into the pouch 100. A right-handed person will normally insert the cord with the left hand and milk with the right hand; this is the reason for placing the pouch 100 to the right of the midline of the drape 10. The invention may also place the pouch on the left side of the midline for use by left-handed people.

Unlike the prior-art syringe method, milking the cord will remove the arterial cord blood as well as the venous blood. Also unlike the prior art, the present invention increases collection efficiency by placing the collecting pouch at a lower elevation, so that gravity assists in collecting the cord blood.

To seal the opening 120 after blood collection, a zip-closure 122 is the preferred closure means. Such zip closures are commonly used on plastic food bags. The most suitable type for the present invention is that having a movable zipper closure element that joins the two edges of zip-seal as it is moved along the length of the seal. Other linear closures may be used.

Figure 4:
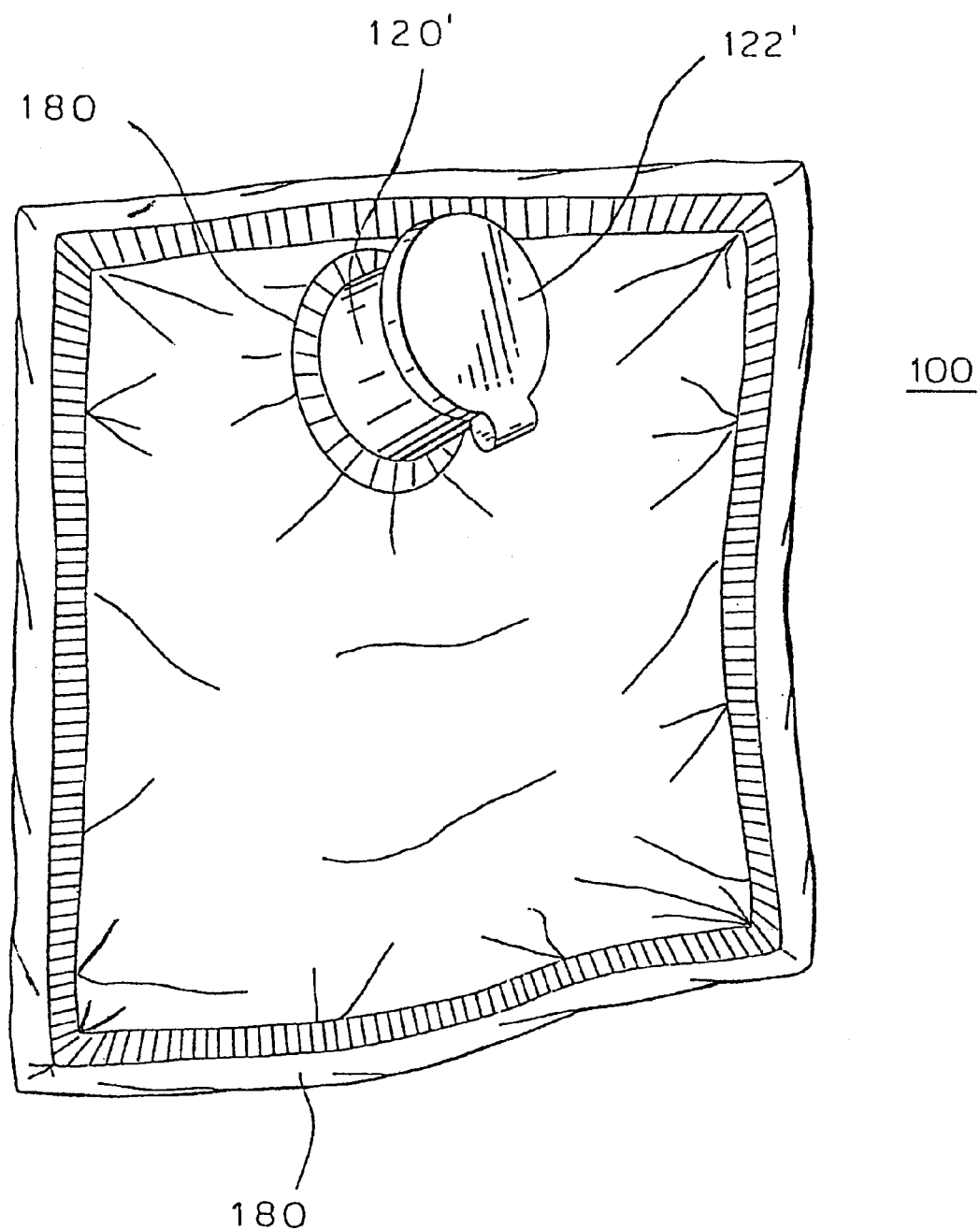
FIG. 4 is a perspective view of still a further embodiment of the pouch.

An alternative closure means is a round hollow spigot 120' with a cap 122' that screws on or snaps on to the spigot (shown in FIG. 4). Such a structure can provide additional resistance to spurting. Flaccid-skin structures with snap-on plastic caps can be very rugged, as shown by commercially-available flaccid wine containers which can even be stepped on without any damage or leakage. FIG. 4 shows such a pouch 100' with welded seams 180 around the pouch perimeter and the spigot base. The pouch 100 may be attached to the drape with an adhesive strip on the back side (not shown in FIG. 4).

If a spigot and cap are used, the spigot 120' may be used as a canal to guide and hold the umbilical cord. The opening, cap 122' and/or spigot 120' may be covered by a flap (not shown in FIG. 4) or the cap may be designed to prevent contamination of the opening.

Graduated indicia 170 may be printed on the side of the pouch 100 to show the amount of cord blood collected.

To prevent coagulation of the cord blood, the pouch 100 preferably contains pellets 160 of freeze-dried citrate-heparin, lithium-heparin, EDTA-heparin, or any conventional anti-coagulant. The anti-coagulant may be liquid instead of solid.

Figure 2:
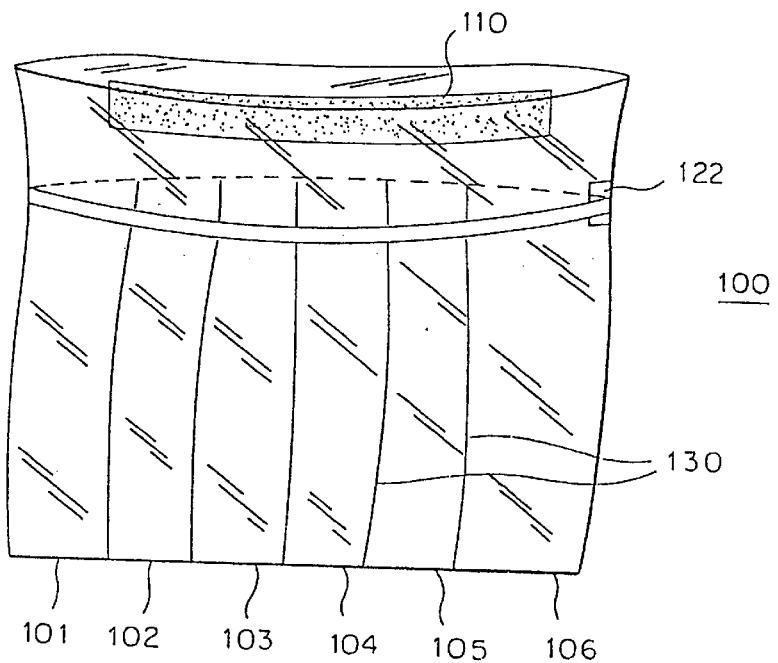
FIG. 2 is a perspective view of a second preferred embodiment of the invention with multiple compartments.

FIG. 2 shows a second preferred embodiment of the present invention, in which the pouch 100 is sub-divided into multiple compartments 101, 102, . . . 106 by seams 130, which are preferably welded seams. The opening 120 is above the seal 122 in this embodiment, and the space between the opening 120 and the compartments 101–106 acts as a manifold to distribute the cord blood. The seal 122 extends across at the tops of the compartments so that when the seal 122 is closed the compartments will be mutually separated. The compartments might contain, for example: citrate-heparin for blood intended for cryopreservation; lithium-heparin pellets for a blood gases analysis sample; EDTA-heparin for non-clotting blood; culture media; or any other substance that might make the cord blood usable for a special purpose. A compartment can also be left empty. FIG. 2 does not show any flap, but the embodiment of this figure preferably also includes a flap over the opening 120. The pouch 100 may also be constructed such that after filling each of the compartments 130 and sealing the top of the compartments, the compartments may be separated from one another, for example to be sent to different testing laboratories.

The device of the invention includes (1) both a one-piece, combined drape and attached pouch or pouches, (2) a kit comprising drape and a pouch including some means for removably attaching the pouch to the drape (e.g., tacky adhesive), and (3) the pouch alone.

The present invention has numerous advantages over the prior-art methods and apparatus. It collects much more of the life-saving cord blood than any previous method; it is economical because it uses a minimum of material and creates no medical waste; it is safe because it does not use breakable glass containers and requires no needles; it is simple and easy, as it needs no table space, there is no apparatus to set out, and the entire collection procedure is as quick and simple as is possible.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation. The industrial applicability is in medical obstetrical procedures. The problems solved by the invention are spillage and leakage of cord blood and undue effort in collecting it.

What is claimed is:

1. An obstetrical method for collecting umbilical cord blood from an umbilical cord after a mother gives birth, the method comprising:

disposing the obstetrical drape onto an obstetrical table with one end below the buttocks of the mother and the other end depending from the end of the table;

providing a collection pouch, the pouch including a sealable opening into the pouch with a sterility flap covering the opening of the pouch, the pouch being removably mounted on the drape at an elevation lower than the tabletop;

after a birth, severing the umbilical cord at an incision distal to the placenta to create an umbilical cord end;

raising the sterility flap;

inserting the cord end into an opening of the pouch;

milking the umbilical cord to inject cord blood into the pouch;

sealing the pouch; and removing the pouch from the drape.

2. The method according to claim 1, further including the step of disinfecting a surface of the umbilical cord adjacent the incision prior to severing.

* * * * *